(12) United States Patent
Kim

(10) Patent No.: US 7,225,053 B2
(45) Date of Patent: May 29, 2007

(54) INFORMATION INPUT DEVICE FOR TABLET AUTOMATIC PACKING MACHINE

(75) Inventor: Jun-ho Kim, Dalseo-Gu (KR)

(73) Assignee: JVM Co., Ltd., Daegu (KR)

( * ) Notice: Subject to any disclaimer, the term of this patent is extended or adjusted under 35 U.S.C. 154(b) by 76 days.

(21) Appl. No.: 11/188,702

(22) Filed: Jul. 26, 2005

(65) Prior Publication Data

US 2005/0256609 A1 Nov. 17, 2005

Related U.S. Application Data

(63) Continuation-in-part of application No. 11/003,406, filed on Dec. 6, 2004.

(30) Foreign Application Priority Data

| Jan. 10, 2004 | (KR) | .................. 10-2004-0001856 |
| Jan. 10, 2004 | (KR) | .................. 10-2004-0001857 |

(51) Int. Cl.
*G06F 17/00* (2006.01)

(52) U.S. Cl. .................. 700/241; 700/242; 700/243; 700/244

(58) Field of Classification Search ................ 700/213, 700/225, 231, 240, 241–244; 221/9; 235/385; 53/396

See application file for complete search history.

(56) References Cited

U.S. PATENT DOCUMENTS

| 4,504,153 | A | * | 3/1985 | Schollmeyer et al. ......... 368/10 |
| 5,671,592 | A | * | 9/1997 | Yuyama et al. ................ 53/493 |
| 5,709,063 | A | * | 1/1998 | Yuyama et al. ................ 53/154 |
| 5,765,606 | A | * | 6/1998 | Takemasa et al. .......... 141/104 |
| 5,930,145 | A | * | 7/1999 | Yuyama et al. ............. 700/231 |
| 6,012,602 | A | * | 1/2000 | Yuyama et al. ............. 221/130 |
| 6,349,848 | B1 | * | 2/2002 | Uema et al. .................... 221/6 |
| 6,380,858 | B1 | * | 4/2002 | Yarin et al. .............. 340/573.1 |
| 6,405,893 | B1 | * | 6/2002 | Tobe et al. ..................... 221/2 |
| 6,471,088 | B1 | * | 10/2002 | Uema et al. .................... 221/4 |
| 6,471,090 | B1 | * | 10/2002 | Inamura et al. ............. 221/124 |
| 6,497,339 | B1 | * | 12/2002 | Geltser et al. ................ 221/13 |
| 6,529,446 | B1 | * | 3/2003 | de la Huerga ................ 368/10 |
| 6,554,157 | B2 | * | 4/2003 | Geltser et al. .............. 221/200 |
| 6,592,005 | B1 | * | 7/2003 | Coughlin et al. ........... 221/129 |
| 6,928,790 | B2 | * | 8/2005 | Takahashi et al. ............ 53/247 |
| 6,957,126 | B2 | * | 10/2005 | Kim .......................... 700/244 |
| 7,080,755 | B2 | * | 7/2006 | Handfield et al. ............ 221/13 |
| 2003/0074868 | A1 | * | 4/2003 | Yasuoka et al. .............. 53/493 |
| 2003/0183642 | A1 | * | 10/2003 | Kempker, Sr. ................ 221/2 |
| 2004/0158349 | A1 | * | 8/2004 | Bonney et al. ............. 700/231 |

* cited by examiner

*Primary Examiner*—Khoi H. Tran
(74) *Attorney, Agent, or Firm*—Oblon, Spivak, McClelland, Maier & Neustadt, P.C.

(57) ABSTRACT

Disclosed is an information input device for a tablet automatic packing machine capable of easily and directly storing tablet information in a memory chip and updating/reading the tablet information in/from the memory chip at a user side.

11 Claims, 9 Drawing Sheets

INFORMATION INPUT DEVICE FOR TABLET AUTOMATIC PACKING MACHINE

RELATED APPLICATIONS

This application claims priority from and is a continuation-in-part (CIP) of U.S. patent application, Ser. No. 11/003,406, filed Dec. 6, 2004, and entitled "INFORMATION INPUT DEVICE FOR TABLET AUTOMATIC PACKING MACHINE", the disclosure which is incorporated herein by reference.

BACKGROUND OF THE INVENTION

1. Field of the Invention

The present invention relates to a tablet automatic packing machine, and more particularly to an information input device for a tablet automatic packing machine capable of easily and directly storing tablet information in a memory chip installed to the tablet automatic packing machine and updating/reading the tablet information in/from the memory chip at a user side.

2. Description of the Related Art

Generally, tablet automatic packing machines serve to dispense corresponding tablets based on prescription data and to automatically pack them based on a dose of tablet. The construction of such a table automatic packing machine is described in detail with reference to FIG. 1.

FIG. 1 is a cross-sectional view illustrating a state in which tablet cassettes are collected in a tablet automatic packing machine according to the prior art. As shown in the drawing, the tablet automatic packing machine 50 includes a plurality of shelves on the upper side of a case 52 shaped as a frame. Each of the plurality of shelves has a plurality of cassette supporters 60 installed thereon for mounting a plurality of tablet cassettes 70, respectively.

The case 52 has a hopper 56 thereunder, which collects tablets discharged from the plurality of cassettes 70 through the plurality of cassette supporters 60. The hopper 56 has a packing assembly 57 thereunder, which packs the collected tablets based on dosage units. Here, the packing assembly 57 includes a printing unit for printing information on each packing paper on which user should note instructions for taking the tablets, and a heater 58 for heat-sealing openings of the packing papers.

FIG. 2 is a view illustrating a state in which tablet cassettes are installed to cassette supporters for the prior art tablet automatic packing machine. If the prior art tablet automatic packing machine determines that the quantity of tablets in a tablet cassette 20 is less than a predetermined value, a tablet cassette tag label 20a attached to one side of the tablet cassette 20 indicates tablet depletion therein in a light emission fashion. Here, a user separates a corresponding tablet cassette from a corresponding tablet supporter 10 and refills corresponding tablets therein. After wards, the user inserts the refilled tablet cassette 20 into the cassette supporter 10 based on recognition of the tablet cassette tag label 20a and the cassette supporter tag label 10a.

FIG. 3 is a cross-sectional view illustrating a state in which a tablet cassette is separated from a cassette supporter for a tablet automatic packing machine according to the first embodiment of the prior art. The tablet cassette 70 has a rotor 72 for guiding and dispensing corresponding tablets, which is installed therewithin, a memory chip 75 and a socket 77 electrically connected to the memory chip 75, which are installed on the lower surface of the table cassette 70. The tablet cassette supporter 60 includes a motor 64 for rotating the rotor 72, which is installed therewithin, and a tablet discharging unit 62 for discharging tablets. The tablet discharging unit 62 includes a tablet discharging hole formed therein and a sensor unit 66 formed around the tablet discharging hole. The sensor unit 66 includes a light reception unit 66a and light emitting unit 66b such that they can perform a sensing operation for tablets discharged through the discharging hole. Also, the tablet cassette supporter 60 includes a connector 67 installed on the upper surface thereof. A passage 54 for downwardly dispensing tablets discharged from the cassette supporter 60 through the tablet discharging unit 62 is formed in the inside of the case 52.

In the case that the table cassette 70 is coupled to the tablet cassette supporter 60, the socket 77 mounting the memory chip 75 thereon is connected to the connector 67 of the tablet cassette supporter 67 such that tablet information stored in the memory chip 75 can be transmitted to a controlling unit (not shown) of the tablet automatic packing machine. Therefore, since a memory chip 75 storing information of tablets contained in a tablet cassette 20 can be connected to a connector of any of the tablet cassette supporters, the tablet cassette and the tablet cassette supporter need not to be assembled so that their tag labels are consistent with each other.

FIG. 4 is a cross-sectional view illustrating a state in which a tablet cassette is separated from a cassette supporter for a tablet automatic packing machine according to the second embodiment of the prior art. The configuration of FIG. 4 employs the same reference numerals as those of FIG. 3 with respect to the same elements. Since a socket 68 electrically connected to a memory chip 65 is directly mounted on the tablet cassette supporter 60, the tablet cassette 70 must be coupled to the tablet cassette supporter 60 while their tag labels are consistent with each other. Before the tablet automatic packing machines constructed as described above are sold, information of tablets to be contained in the tablet cassettes, such as tablet information, tablet cassette identification number, tablet name, sensitivity/minimum sensing time/sensing period etc. of a sensor for sensing tablet discharge, is recorded in each of the memory chips installed in the automatic packing machines by an exclusive input device. However, as a variety of new tablets have been developed, tablet information must be frequently updated or newly stored in the memory chips.

However, there is no known separate input device for storing/updating tablet information to the respective memory chips. Therefore, if there is a need to update information stored in the respective memory chips of the respective cassette supporters, the prior art tablet automatic packing machine must be sent to the manufacturer or a sales agency. Accordingly, the prior art tablet automatic packing machine has disadvantages in that the update procedure is complicated, and update of tablet information stored in the memory chip is delayed. Also, since it must be sent to the manufacturer or a sales agency to update tablet information, the dispenser cannot dispense the tablets according to prescription data using the prior art tablet automatic packing machine because it is being updated.

Also, the prior art tablet automatic packing machine doesn't provide the user with the convenience of being able to easily confirm tablet information stored in the memory. In addition, if it is difficult to recognize tablet information through tag labels 10a and/or 20a attached to a cassette supporter 10 and/or tablet cassette 20, the user must find, one by one, the cassette supporter 10 having a memory chip storing corresponding information of tablets contained in the tablet cassette 20.

SUMMARY OF THE INVENTION

Therefore, the present invention has been made in view of the above problems, and it is an object of the present invention to provide an information input device for a tablet automatic packing machine capable of easily and directly storing tablet information in a memory chip and updating/reading the tablet information in/from the memory chip at a user side.

In accordance with an aspect of the present invention, the above object can be accomplished by the provision of an information input device for a tablet automatic packing machine including a plurality of cassette supporters, in which each cassette supporter has a first connector on the upper surface thereof and a memory chip which is mounted and electrically connected on and to the first connector, comprising a second connector separatably connected to the first connector electrically connected to the memory chip, an input unit for inputting tablet information to be stored in the memory chip, a storage unit for storing a tablet information input program and associated data, a main controlling unit for inputting the tablet information from the input unit according to execution of the tablet information input program stored in the storage unit and for outputting the tablet information and a recording control command for enabling the tablet information to be stored in the memory chip and a recording unit for recording the tablet information in the memory chip electrically connected to the first and second connectors according to the recording control command inputted from the main controlling unit.

Accordingly, a user can easily and directly update tablet information stored in each memory chip installed in the tablet automatic packing machine.

In accordance with another aspect of the present invention, there is provided an information input device for a tablet automatic packing machine including a plurality of tablet cassettes, in which each tablet cassette has a first connector on the lower surface thereof and a memory chip which is mounted and electrically connected on and to the memory chip, comprising a second connector separatably connected to the first connector electrically connected to the memory chip, an input unit for inputting tablet information to be stored in the memory chips, a storage unit for storing a tablet information input program and associated data, a main controlling unit for inputting the tablet information from the input unit according to execution of the tablet information input program stored in the storage unit and for outputting the tablet information and a recording control command for enabling the tablet information to be stored in the memory chip and a recording unit for storing the tablet information in the memory chip electrically connected to the first and second connectors according to the recording control command inputted from the main controlling unit.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

With reference to the attached drawings and the embodiments of the present invention, a detailed description of the present invention is described below, such that the present invention and the embodiments thereof can be easily understood and implemented by those skilled in the art.

Figure 5:
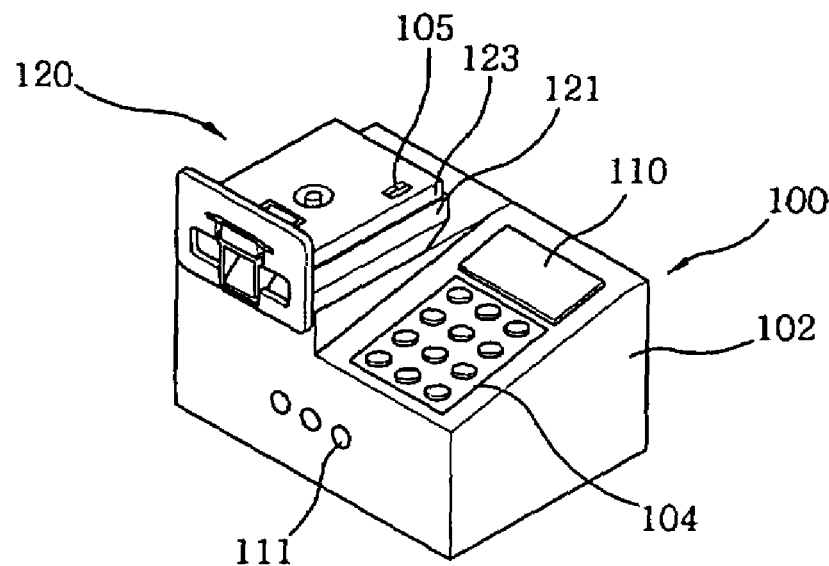
FIG. 5 is a perspective view illustrating an information input device for a tablet automatic packing machine according to one embodiment of the present invention.

FIG. 5 is a perspective view illustrating an information input device for a tablet automatic packing machine according to one embodiment of the present invention. The information input device of a tablet automatic packing machine is used for directly updating tablet information stored in each memory chip installed in each table cassette, respectively, at a user side.

Figure 1:
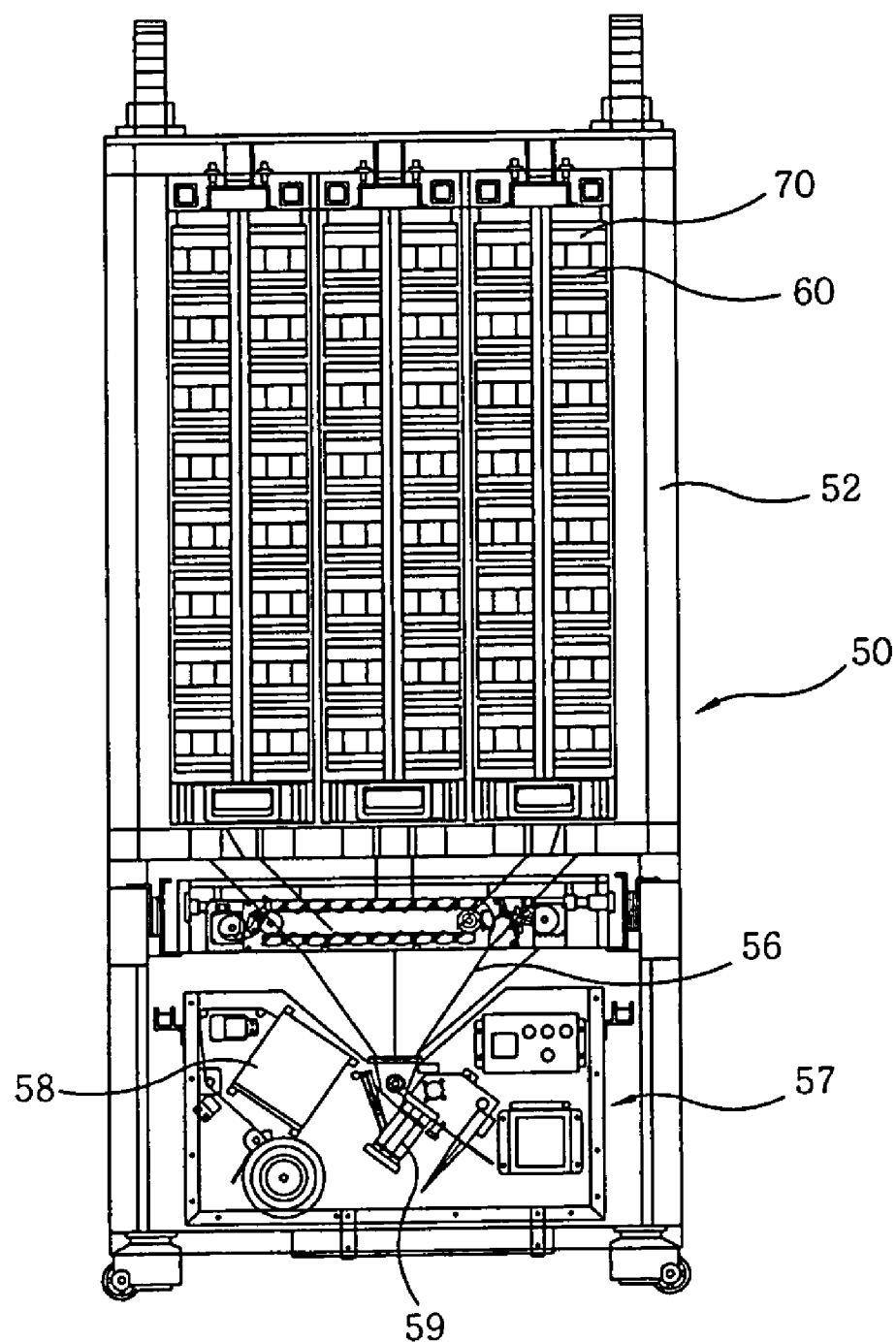
FIG. 1 is a cross-sectional view illustrating a state in which tablet cassettes are collected in a tablet automatic packing machine according to the prior art.
Figure 2:
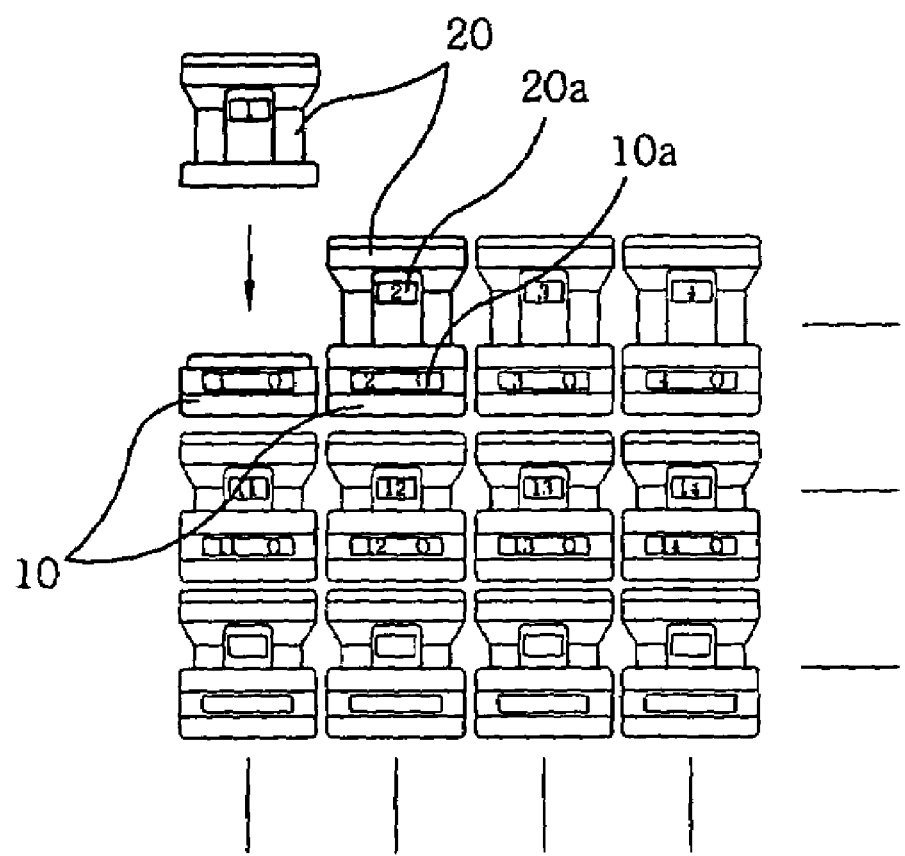
FIG. 2 is a view illustrating a state in which tablet cassettes are installed to cassette supporters for the prior art tablet automatic packing machine.
Figure 3:
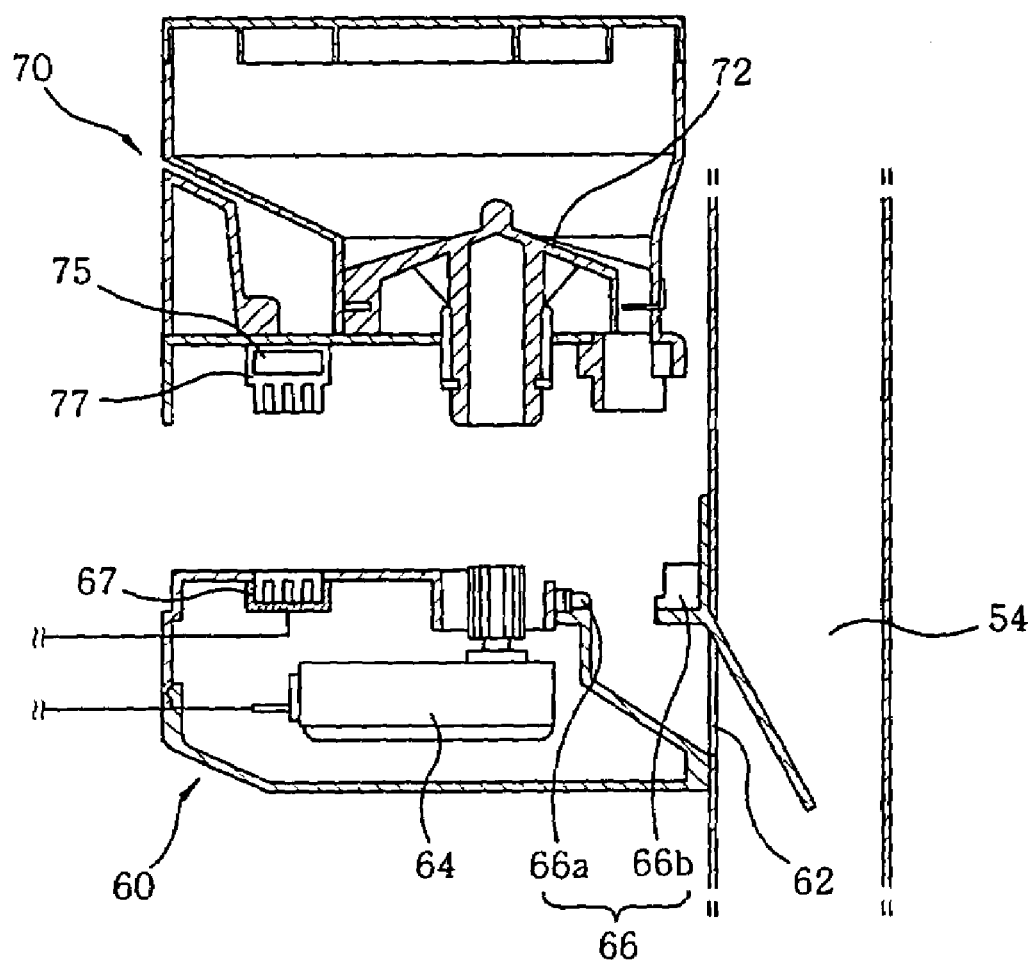
FIG. 3 is a cross-sectional view illustrating a state in which a tablet cassette is separated from a cassette supporter for a tablet automatic packing machine according to the first embodiment of the prior art.
Figure 4:
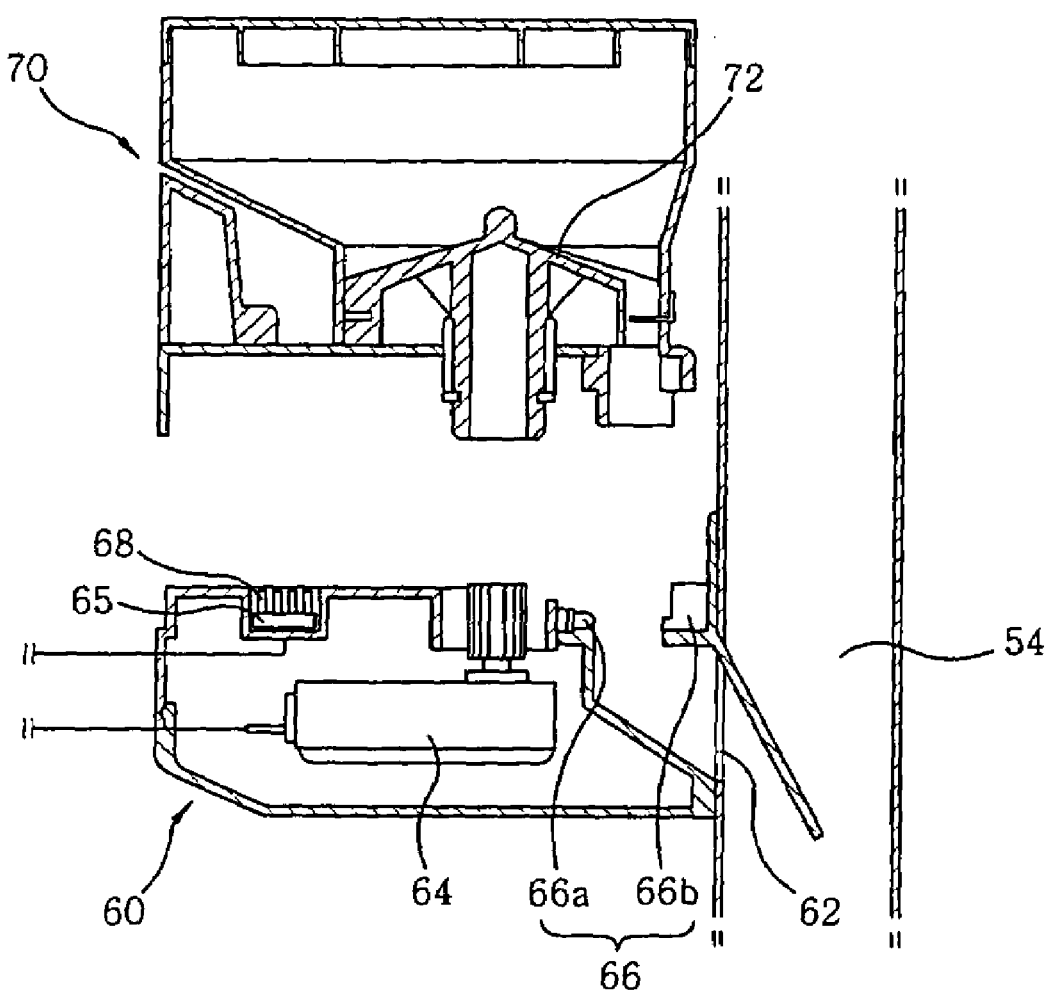
FIG. 4 is a cross-sectional view illustrating a state in which a tablet cassette is separated from a cassette supporter for a tablet automatic packing machine according to the second embodiment of the prior art.

The information input device 100 includes a body 102 forming its external shape. In one side of the upper surface of the body 102 a cassette mounting unit 120 is formed such that it can be separatably coupled to a table cassette. In the embodiment, the cassette mounting unit 120 includes a matching unit 121 on which a second connector 105 is formed such that it can be connected to and separated from the socket 77 of the tablet cassette as shown in FIG. 3 and a guiding unit 123 for guiding the tablet cassette along sides of the matching unit 121 to a matching position of the tablet cassette. The cassette mounting unit 120 may be integratedly or separatably implemented with the body 102.

Also, on the other side of the upper surface of the body 102 an input unit 104 for inputting information to be stored in the memory chip of the tablet cassette by user manipulation and a display unit 110 for displaying tablet information inputted from the input unit 104 are formed. In addition, operation state display lamps 111 are installed in the side of the body 102 so that they can display operations states of the information input device 100. The input unit 104 is preferably implemented with a keypad including numeral keys and function keys etc. though, it may be further implemented with a touch panel, an italic font input unit, voice recognition unit, etc. The display 110 is preferably implemented with a Liquid Crystal Display (LCD). Also, the operation state displaying lamps 111 are preferably implemented with Light-Emitting Diodes (LEDs). Even though the preferred embodiment of the present invention describes that the input unit, the display unit and the operation state display lamps are installed in the specific positions of the body as mentioned above, they may be installed to the body in other fashions with their installation positions changed.

Figure 6:
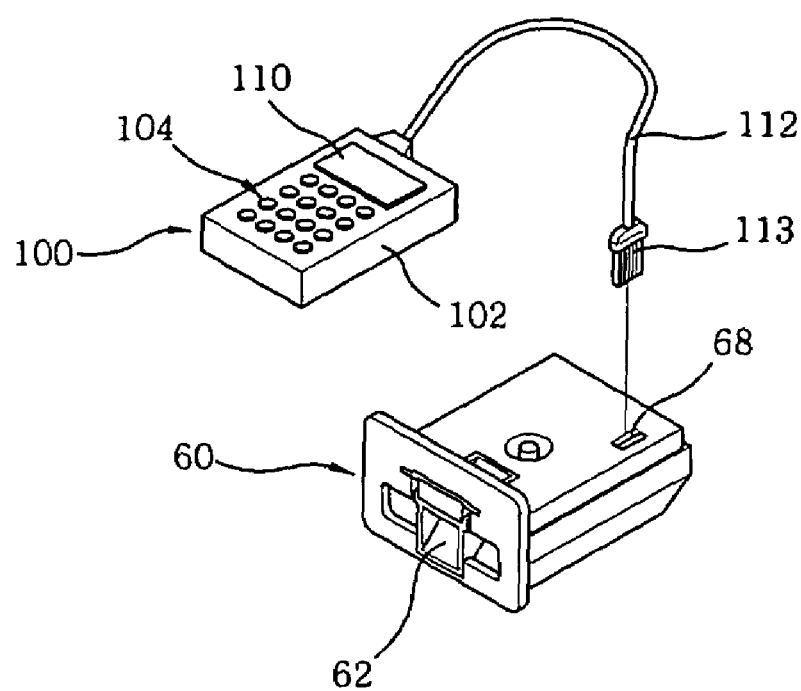
FIG. 6 is a perspective view illustrating an information input device of a tablet automatic packing machine according to another embodiment of the present invention.

FIG. 6 is a perspective view illustrating an information input device of a tablet automatic packing machine according to another embodiment of the present invention. The information input device of a tablet automatic packing machine is used for directly updating tablet information stored in each memory chip installed in each tablet cassette supporter 60, respectively, at a user side.

The information input device 100 includes an input unit 104 for inputting information to be stored in a memory chip installed in the tablet cassette supporter 60, a display unit 110 for displaying tablet information inputted to the input unit 104 and a connection cable 112 for electrically connecting the information input device 100 to the tablet cassette supporter 60, in which one end of the connection cable 112 has a connector 112 to be electrically connected to the socket 68 connected to the memory chip. Here, the input unit 104 and the display unit 110 are installed on a body 102 forming the external shape of the information input device.

Figure 7:
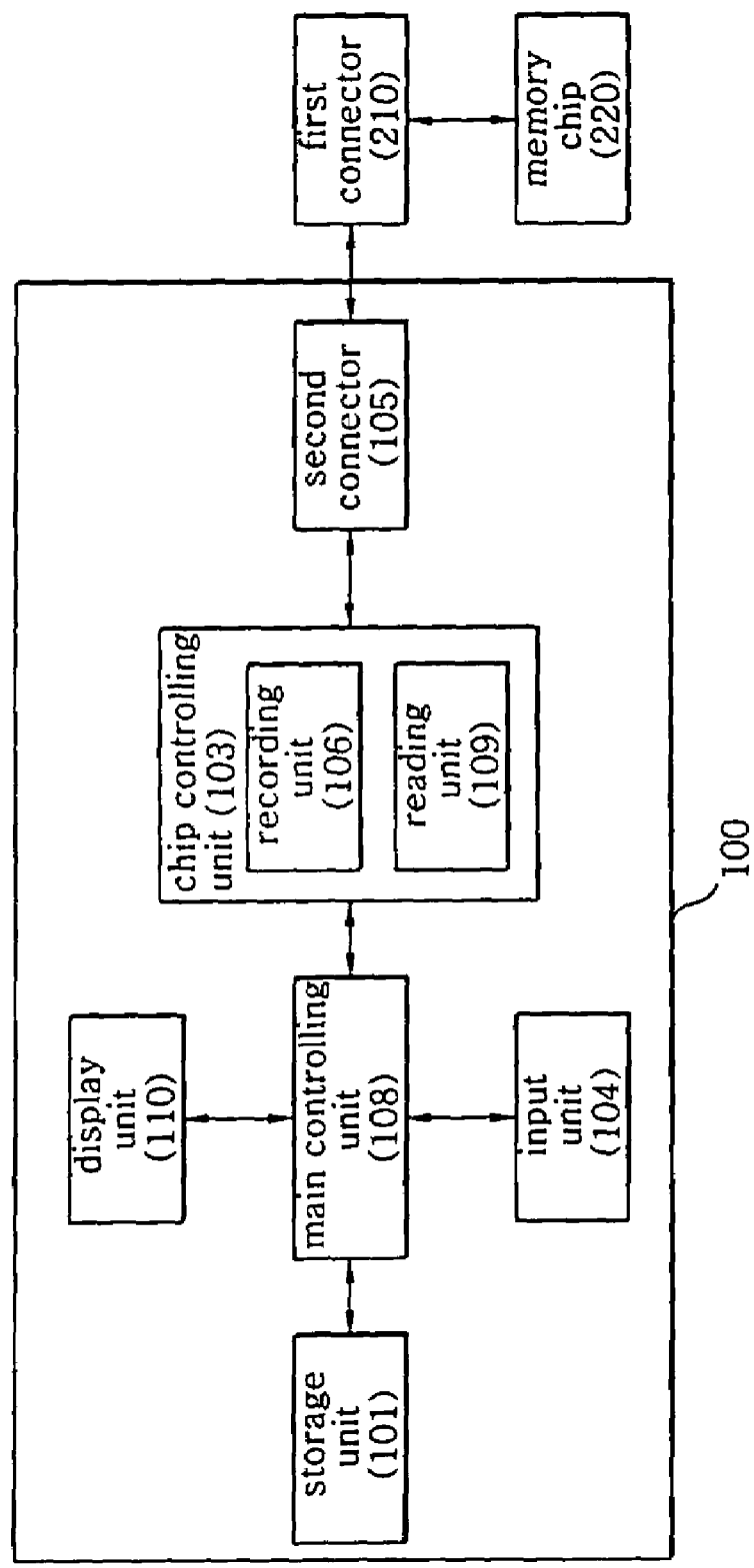
FIG. 7 is a block diagram illustrating an information input device of a tablet automatic packing machine according to the present invention.

FIG. 7 is a block diagram illustrating an information input device for a tablet automatic packing machine according to the present invention. As shown in the drawing, the information device includes a storage unit 101, a chip controlling unit 103, an input unit 104, a second connector 105, a main controlling unit 108 and a display unit 110.

The storage unit 101 stores a tablet information input program and associated data and preferably is implemented with a flash memory. Also, the storage unit 101 further stores a tablet cassette identification number, tablet name, sensitivity/minimum sensing time/sensing period of a sensor for sensing tablet discharge.

The input unit 104 inputs information to be recorded in a memory chip 220 and is preferably implemented with a general keypad. Also, the input unit 104 may be further implemented with a touch panel, an italic font input unit, and a voice recognition unit, etc.

The second connector 105 is separatably connected to the first connector 210 connected to the memory chip 220. The memory chip 220 may be installed in the table cassette or a tablet cassette supporter.

The main controlling unit 108 controls the entire system and is preferably implemented with a microprocessor in which ROMs, RAMs and peripheral elements associated therewith are integrated. The main controlling unit 108 inputs tablet information from the input unit 104 according to execution of the tablet information input program stored in the storage unit 101 and outputs the tablet information and a recording or reading control command for storing or reading the tablet information in or from the memory chip.

The chip controlling unit 103 according to one embodiment of the present invention includes a recording unit 106 for storing tablet information in the memory chip 220 connected to the first and second connection unit 210 and 105 according to the recording control command of the main controlling unit 108. The chip controlling unit 103 according to the another embodiment of the present invention further includes a reading unit 109 for reading out the tablet information stored in the memory chip 220 connected to the first and the second connection unit 210 and 105 according to the reading out control command for the main controlling unit 108.

Figure 8:
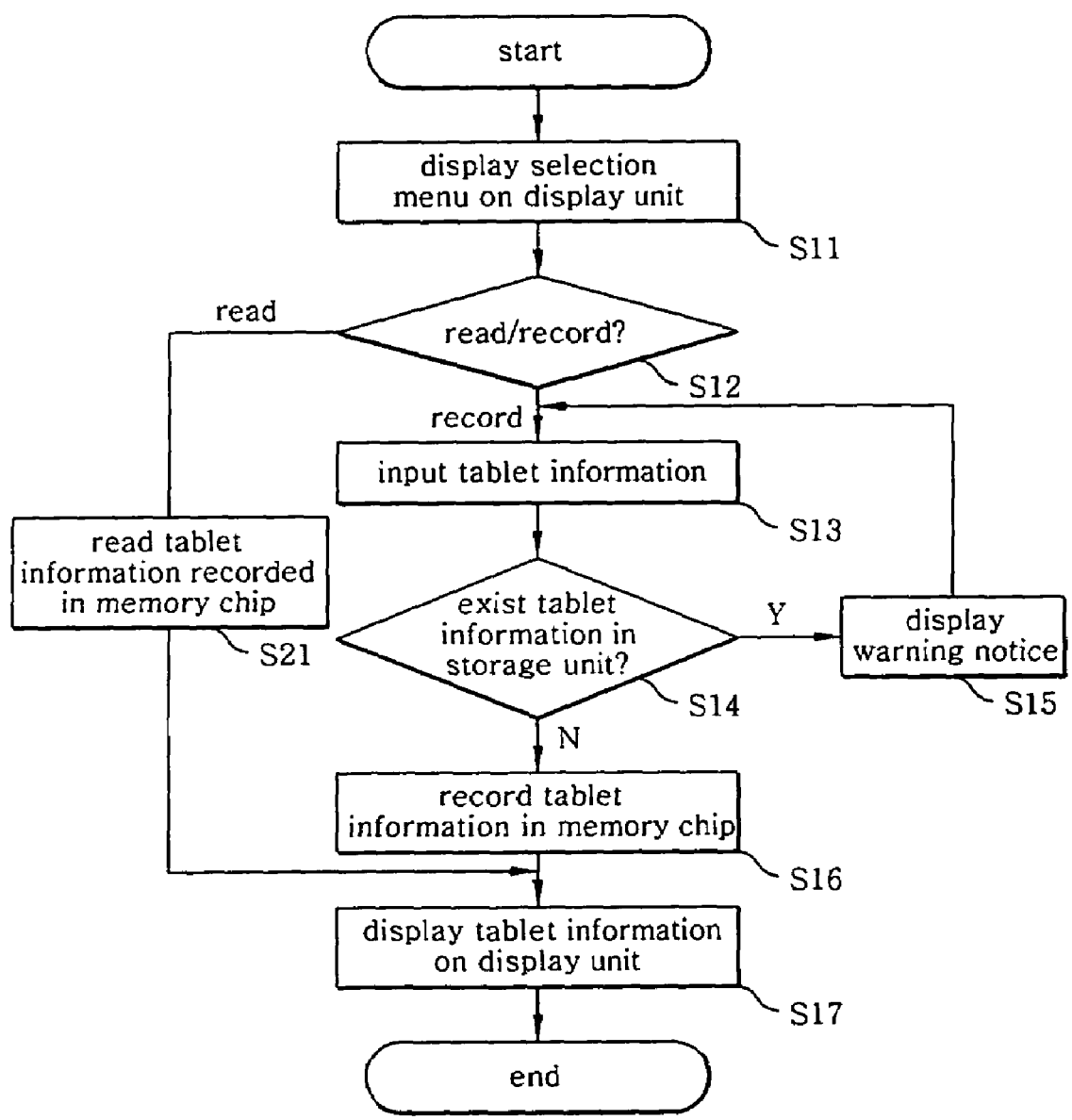
FIG. 8 is a flow chart describing an operating method of an information input device for a tablet automatic packing machine according to the present invention.

FIG. 8 is a flow chart describing an operating method of an information input device for the tablet automatic packing machine according to the present invention. A detailed description of the information input device of the present invention is described such that it reads tablet information of the memory chip installed in the tablet cassette or records the tablet information in the memory chip.

Firstly, each of the respective tablet cassettes is precisely mounted on a predetermined position through a guiding unit (123 of FIG. 5) formed in the matching unit (121 of FIG. 5). After that, a socket (77 of FIG. 3) of the memory chip (75 of FIG. 3) installed on the lower surface of the tablet cassette (70 of FIG. 3) is electrically connected to the second connector (105 of FIG. 5).

When the tablet cassette is placed on the cassette mounting unit (120 of FIG. 5) of the information input device, the information input device displays a menu on the display unit (110 of FIG. 5). After that, the information input device determines whether selection information for reading or storing tablet information from or in the memory chip is inputted in steps S11 and S12.

When selection information for a recording menu is selected in the information input device, the display unit (110 of FIG. 5) displays the recording menu thereon and the input unit (104 of FIG. 5) inputs tablet information such as sensitivity/minimum sensing time/sensing period of a sensor for sensing tablet discharge, tablet cassette identification number, tablet name, etc. therethrough in step S13.

After that, the information input device determines whether the tablet cassette identification number has already been allocated or the tablet information inputted in step S13 is used. If the determination is positive, a warning display signal is outputted on the display unit (110 of FIG. 5) in steps S14 and S15.

On the other hand, if the tablet cassette identification number has already been allocated but the tablet information inputted in step S13 is not used, tablet information for the tablet cassette is stored in the memory chip in step S16 and the display unit (110 of FIG. 5) displays the tablet information stored in the memory chip thereon such that the user can recognize the displayed tablet information in step S17.

Meanwhile, if selection information for a readout menu is inputted in the information input device, tablet information stored in the memory chip of the tablet cassette is read out therefrom in step S21. After that, the display unit (110 of FIG. 5) displays the read tablet information thereon is step S17, and then the user can refill corresponding tablets in the tablet cassette or confirm whether the tablet information is correctly stored in the memory chip based on the confirmation of the tablet information displayed on the display unit (110 of FIG. 5).

Figure 9:
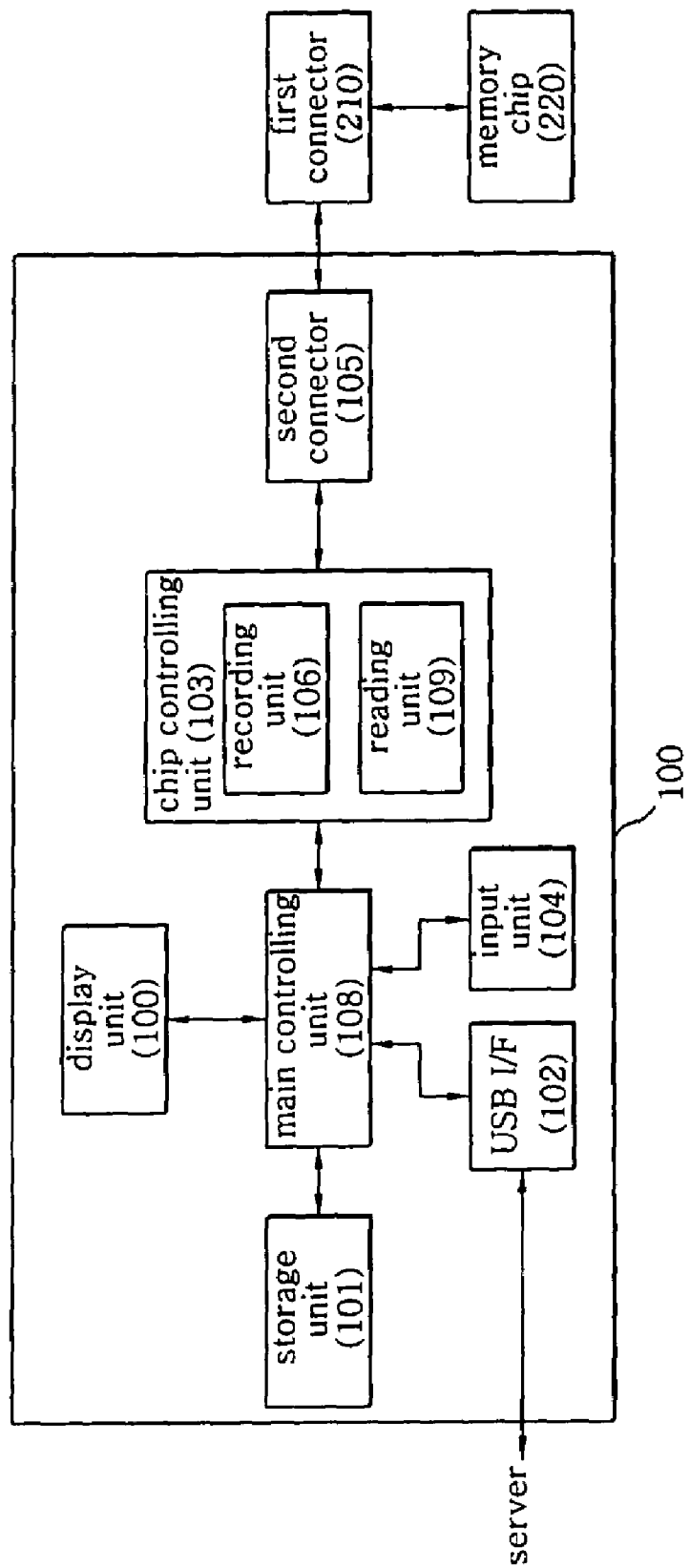
FIG. 9 is a block diagram illustrating an information input device of a tablet automatic packing machine according to another embodiment of the present invention.
Figure 10:
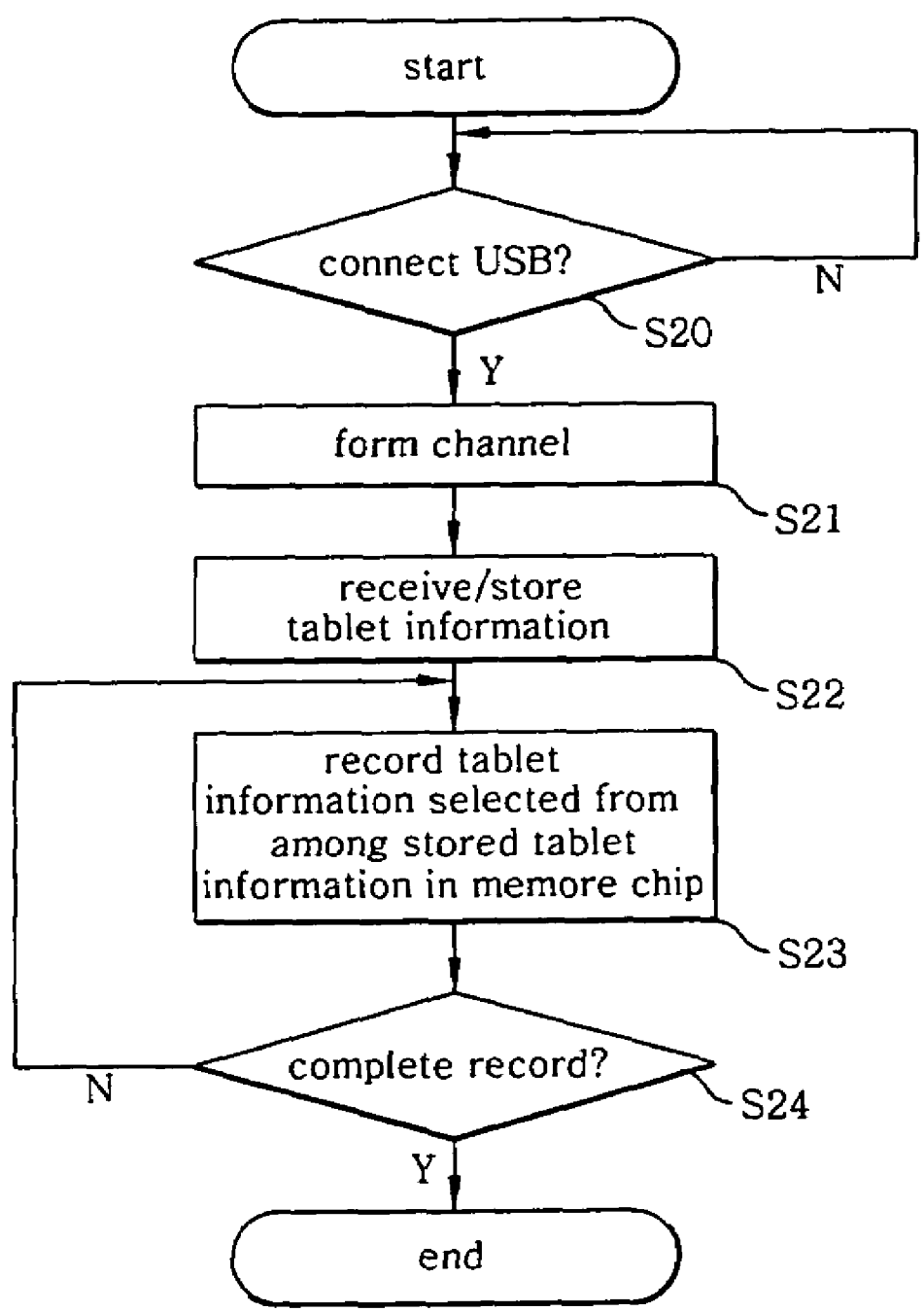
FIG. 10 is a flow chart describing an operating method of the information input device shown in FIG. 9.

FIG. 9 is a block diagram illustrating an information input device of a tablet automatic packing machine according to another embodiment of the present invention, and FIG. 10 is a flow chart describing an operating method of the information input device shown in FIG. 9.

Firstly, the configuration of the information input device of FIG. 9 is identical to that of FIG. 7, except that the device further includes a USB interface unit 102 for inputting tablet information from a server, and thus the main controlling unit 108 is differently operated to that of FIG. 7. Namely, the main controlling unit 108 stores the tablet information received through the USB interface unit 102 in the storage unit 101 and then records the stored tablet information in the memory chip which is in a tablet cassette or a cassette supporter. More specifically, the USB interface unit 102 and the main controlling unit 108 are described below.

The main controlling unit 108 stores the tablet information received through the USB interface unit 102 in the storage unit 101, and outputs the stored tablet information and a record control command for enabling the tablet information to be stored in the memory chip.

On the other hand, the USB interface unit 102 performs USB communication with a server, in which the USB interface unit 102 may be connected to the server via a USB cable. Such a USB interface unit 102 may be implemented with a server PC interface unit for receiving tablet information from the server, and can be replaced with a local area wireless communication means, such as a Bluetooth module.

With reference to FIG. 10, operations of the information input device of FIG. 9 are described in detail below.

Firstly, the information input device of FIG. 9 is connected to the server via a USB cable. When completing such connection, the main controlling unit 108 of the information input device can check a USB connection state in step S20, and, based on the check result, can form a channel with the server in step S21.

When forming a channel with the server, the main controlling unit 108 receives tablet information from the server and stores the received tablet information in the storage unit 101 in step S22. Here, a worker can input tablet cassette number, tablet name, and tablet information, through a data input device of the server, such that they can be registered in the server, and transmit the registered tablet information to the information input device through the USB cable. Here, the table information includes sensitivity/minimum sense time/sensing period of a sensor which can sense tablet discharge.

Therefore, the main controlling unit 108 of the information input device can receive tablet information from a plurality of servers, store them therein and then process them.

On the other hand, when the tablet information is stored therein, the information input device is separated from the server, and then the second connector 105 of the information input device is connected to the first connector of the cassette supporter 60, as shown in FIG. 6. After that, when one of the stored tablet information is requested to be stored, the main controlling unit 108 reads the tablet information selected by the worker from the storage unit 101, and then outputs the read tablet information and a record control command, which enables the tablet information to be stored in the memory chip, to the chip controlling unit 103.

Accordingly, the tablet information selected by the worker can be recorded in the memory chip 220 by the recording unit 106 of the chip controlling unit 103.

Since the information input device according to another embodiment of the present invention can input the tablet information through the server and then record the received information in the memory chip, the worker does not have to register tablet information in the server and then input the tablet information in the information input device again.

As apparent from the above description, the information input device of the tablet automatic packing machine according to the present invention has advantages in that information stored in the memory chip of the tablet cassette can be directly updated or read at a user side.

Also, since information of tablets contained in each of the respective tablet cassettes is relatively easily read, the user can obtain correct information of tablets contained therein such that he/she can easily monitor or manage a stock of tablets.

Now, the construction and operation of the information input device of a tablet automatic packing machine according to another embodiment of the present invention are described in detail below.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An information input device for a tablet automatic packing machine including a plurality of cassette supporters, in which each cassette supporter has a first connector on the upper surface thereof and a memory chip which is mounted and electrically connected on and to the first connector, comprising:
    a second connector separatably connected to the first connector electrically connected to the memory chip;
    a server PC interface unit for receiving tablet information from an external server;
    an input unit for inputting tablet information to be stored in the memory chip;
    a storage unit for storing a tablet information input program and associated data;
    a main controlling unit for storing inputted or received tablet information in the storage unit, and outputting the stored tablet information and a record controlling command for enabling the tablet information to be stored in the memory chip; and
    a recording unit for recording the tablet information in the memory chip electrically connected to the first and second connectors according to the recording control command inputted from the main controlling unit.

2. The information input device as set forth in claim 1, further comprising a display unit for displaying the tablet information inputted from the input unit.

3. The information input device as set forth in claim 1, further comprising a connection cable, both ends of which have connecting terminals such that its one end is connected to the first connector and its other end is connected to the second connector.

4. The information input device as set forth in claim 3, further comprising a display unit for displaying the tablet information inputted from the input unit.

5. The information input device as set forth in claim 4, further comprising a reading unit for reading the tablet information stored in the memory chip electrically connected to the first and second connectors according to a reading control command inputted from the main controlling unit.

6. The information input device as set forth in claim 4, wherein the server PC interface unit is one of a USB interface unit and a Bluetooth module.

7. An information input device for a tablet automatic packing machine including a plurality of tablet cassettes, in which each tablet cassette has a first connector on the lower surface thereof and a memory chip which is mounted and electrically connected on and to the memory chip, comprising:
    a second connector separatably connected to the first connector electrically connected to the memory chip;
    a server PC interface unit for receiving tablet information from an external server;
    an input unit for inputting tablet information to be stored in the memory chips;

a storage unit for storing a tablet information input program and associated data;

a main controlling unit for storing inputted or received tablet information in the storage unit, and outputting the stored tablet information and a record controlling command for enabling the tablet information to be stored in the memory chip; and a recording unit for storing the tablet information in the memory chip electrically connected to the first and second connectors according to the recording control command inputted from the main controlling unit.

8. The information input device as set forth in claim 7, further comprising a display unit for displaying the tablet information inputted from the input unit, and a reading unit for reading the tablet information stored in the memory chip electrically connected to the first and second connectors according to a reading control command inputted from the main controlling unit.

9. The information input device as set forth in claim 7, further comprising a cassette mounting unit formed on one side of the upper surface of a body forming the external shape of the information input device, in which the tablet cassette is separatably connected to the cassette mounting unit, wherein the cassette mounting unit includes:

a matching unit in which a second connector is formed on the upper surface of the body, such that the second connector is separatably connected to the first connector; and a guide unit for guiding the tablet cassette along sides of the matching unit to a predetermined matching position of the matching unit.

10. The information input device as set forth in claim 9, further comprising a display unit for displaying the tablet information inputted from the input unit, and a reading unit for reading the tablet information stored in the memory chip electrically connected to the first and second connectors according to a reading control command inputted from the main controlling unit.

11. The information input device as set forth in claim 10, wherein the server PC interface unit is one of a USB interface unit and a Bluetooth module.

* * * * *